United States Patent [19]

Aliotta et al.

[11] 4,234,339
[45] Nov. 18, 1980

[54] CORROSION-RESISTANT DENTAL ALLOY

[75] Inventors: Joseph Aliotta, Newton, Mass.; Louis F. Alcuri, Matawan, N.J.

[73] Assignee: Engelhard Minerals & Chemicals Corporation, Iselin, N.J.

[21] Appl. No.: 936,669

[22] Filed: Aug. 24, 1978

Related U.S. Application Data

[63] Continuation-in-part of Ser. No. 760,182, Jan. 17, 1977, abandoned.

[51] Int. Cl.³ .............................................. B22F 1/00
[52] U.S. Cl. ......................................... 75/255; 75/251
[58] Field of Search ...................... 75/0.5 R, 251, 255, 75/169, 173 C, 134 N, 134 B, 134 C

[56] References Cited

U.S. PATENT DOCUMENTS

| | | | |
|---|---|---|---|
| 3,841,860 | 10/1974 | Wolf | 75/169 |
| 3,871,876 | 3/1975 | Asgar et al. | 75/169 |
| 3,980,472 | 9/1976 | Asgar et al. | 75/173 C |
| 3,997,327 | 12/1976 | Tolliver et al. | 75/169 |
| 3,997,328 | 12/1976 | Greener | 75/0.5 R |
| 3,997,329 | 12/1976 | Aliotta et al. | 75/169 |
| 3,997,330 | 12/1976 | Aliotta et al. | 75/169 |
| 4,008,073 | 2/1977 | Kropp | 75/169 |
| 4,080,199 | 3/1978 | Sung et al. | 75/0.5 R |

Primary Examiner—L. Dewayne Rutledge
Assistant Examiner—Michael L. Lewis

[57] ABSTRACT

A corrosion-resistant dental alloy is disclosed which has improved handling characteristics during the filling of a dental cavity. The alloy is a substantially uniform blend of three types of particles having the same chemical components, but differing in morphology and, optionally, in proportions of components. One type of particle is spherical or spheroidal in form. The second type of particle is a randomly-shaped microcrystalline form. The third type of particle is a flake-like particle. Handling characteristics of an amalgam prepared from such three particles can be adjusted to suit the requirements of the user by varying the relative proportions of the three types of particles while still retaining the corrosion resistance of the particles.

8 Claims, 4 Drawing Figures

CORROSION-RESISTANT DENTAL ALLOY

CROSS REFERENCE TO RELATED APPLICATIONS

This application is a continuation-in-part of copending application Ser. No. 760,182, filed Jan. 17, 1977, now abandoned.

BACKGROUND OF THE INVENTION

The present invention relates generally to the dental alloys which are used for filling teeth from which decayed portions have been removed. More particularly, the invention relates to a corrosion resistant dental alloy which permits adjusting the handling characteristics of amalgams made with such alloy.

The prior art emphasized the development of alloys which are corrosion resistant. While typical dental alloys are principally composed of silver and tin, they usually contain small amounts of copper and zinc. A typical alloy of the prior art would contain at least 65 wgt.% silver, about 1–2 wgt.% zinc, and about 2–4 wgt.% copper, with the remainder being tin. Such alloys are not completely resistant to corrosion. It has been found that increasing the copper content of such alloys provides increased strength and also avoids the formation of what is known in the art as the gamma-two phase, a tin and mercury phase which has low resistance to corrosion and thus may lead to early deterioration of fillings. Typical of such high copper alloys are those disclosed in U.S. Pat. No. 3,871,876 and U.S. Pat. No. 3,997,328. Such dental alloy compositions increase the copper content from the typical 2–4 wgt.% to the range of 8–27 wgt.% in the first mentioned patent, and in the latter patent, from 20–40 wgt.%.

While such alloys have improved corrosion resistance, another important characteristic of dental alloys has been neglected heretofore. The success of a dentist in filling a dental cavity is related to the handling characteristics of the alloy after it is amalgamated with mercury. For example, the high copper alloy disclosed in U.S. Pat. No. 3,871,876, is typically produced by air atomization from the molten state which results in a spherical or spheriodal form for the finished alloy. It is characteristic of alloys having a spherical shape that they feel relatively soft to the dentist and appear to require delicate handling. They are sometimes difficult to pack into a dental cavity since they have a tendency to be formed up the wall of the cavity if too much pressure is exerted or an instrument is used which has a small bearing area. Consequently, many dentists find that such spherical material is not well-adapted to their individual technique. As a result, they may be unable to take advantage of the corrosion resistance inherent with spherical alloys having a high copper content.

One method of improving handling characteristics of conventional dental alloys is disclosed and claimed in U.S. Pat. No. 3,997,327. In that invention a major portion of spherical particles is combined with a minor portion of microcut irregular particles, or flakes. Typical dental alloys in the prior art generally have been of the flake type, which inherently requires a higher pressure in order to pack it into a dental cavity than is characteristic of the spherical particles. By combining spherical particles with flake particles having the same or a similar composition, it is possible to improve the handling characteristics of the resulting mixture. Such a combination, having a conventionally low copper content, has less resistance to corrosion than the higher copper content alloys previously discussed.

Another method of improving handling characteristics applied to a corrosion resistant alloy is disclosed and claimed in a copending application filed concurrently with the present application in the name of the inventors hereof and assigned to a common assignee, entitled "Corrosion-Resistant Dental Alloy Having Improved Handling Characteristics" (hereinafter "Improved Alloy"). The alloy of U.S. Pat. No. 3,871,876 is produced as particles having a unique randomly-shaped microcrystalline morphology which is characterized by having a higher than average silver and copper content at the surface of the particles than in the interior of the particles and a surface area about 20–30% greater than that of spherical particles and about 20–30% less than that of flake-like particles. The unique form of the particles provides handling characteristics similar to those of flake-like particles, while retaining the corrosion resistance characteristic of the spherical form. Although the unique particles of Improved Alloy are advantageous in providing excellent handling characteristics, fine adjustment of the handling characteristics is not readily made with it.

The present invention has as its objective providing adjustment of handling characteristics of corrosion-resistant dental alloys.

SUMMARY OF THE INVENTION

In accordance with the present invention, there is provided a corrosion-resistant dental alloy mixture for use as a filling for dental cavities after amalgamation with mercury, comprising a substantially uniform mixture of a first corrosion-resistant alloy comprising a mixture of silver, tin and copper, the first alloy being in the form of spherical particles having a mean particle size of from about 20 to 26.5 microns, and further having a particle size distribution such that substantially all of the particles fall within a particle size range of from about 1 to 75 microns. The second corrosion-resistant alloy is included and comprises a mixture of silver, tin and copper, the second alloy having a mean particle size of from about 20 to 26.5 microns, and further having a particle size distribution such that substantially all of the particles fall within a particle size range of from about 1 to 75 microns. These particles have a surface area ranging from about 0.23 to 0.26 $m^2/gm$. A third alloy is also included and comprises a mixture of silver, tin and copper, the third alloy comprising flake-like particles having a mean particle size of between about 25 and 30 microns, and further having a particle size distribution such that substantially all of these particles fall within a particle size range of from about 1 to 75 microns. These particles have a surface area of about 0.33 $m^2/gm$, and comprise not more than about 25% by weight of the dental alloy mixture.

In accordance with one aspect of the invention, the first and said second alloys comprise from about 47 to 70 percent by weight of silver, from about 20 to 32 percent by weight of tin, and from about 7 to 27 percent by weight of copper and the third alloy comprises from about 55 to 75 percent by weight of silver, from about 20 to 40 percent by weight of tin, and up to about 10 percent by weight of copper. The first and second alloys need not be identical to each other, so long as they fall within the above range.

One aspect of the invention provides that corrosion-resistant dental alloy comprises a mixture of from about 25 to 60 percent by weight of the first alloy, from about 25 to 60 percent by weight of the second alloy, and from about 10 or 15 to 25 percent by weight of the third alloy.

The invention also provides for a dental amalgam comprising a combination of the above corrosion-resistant dental alloy with mercury, preferably one comprising about 1 part by weight of mercury for each part by weight of corrosion-resistant dental alloy.

The first, second and third particles are each sized such that at least about 90% by weight thereof fall within a particle size range of from about 10 to 52 microns, in accordance with another aspect of the invention.

Generally, the dental alloy of the invention combines corrosion resistance, in that it has a relatively high copper content, and good handling qualities. The alloy is composed of a mixture of three forms of particles. The compositions of two of the forms of particles correspond generally to that of the spherical material disclosed in United States patent 3,871,876, being within the range of about 47% to 70% by weight silver, 20% to 32% by weight tin, and 7% to 27% by weight copper. As is true of the material of the 3,871,871 patent, the two forms of particles may have a higher than average silver and copper content at the surface of the particles, but while one particle is spherical, the second particle has the unique form of Improved Alloy. The third type of particle has the relatively low copper and high silver content typical of the prior art. In a preferred embodiment, the third type of particles will have a composition of about 55% to 75% by weight silver, 20% to 40% by weight tin, 0% to 10% by weight copper and 0% to 2% by weight zinc. By combining suitable proportions of spherical particles, randomly-shaped microcrystalline particles, and flake-like particles, the handling characteristics of amalgams prepared from such mixtures can be adjusted to suit the requirements of the individual user. Although any suitable proportions of the first and second types of particles may be employed, the third type of particle is limited to a maximum of 25% by weight of the alloy mixture in order to retain the corrosion resistance provided by the first and second types of particles.

DESCRIPTION OF THE PREFERRED EMBODIMENTS

A dentist in packing an amalgam prepared from a dental alloy and mercury into a dental cavity considers two factors to be of particular importance. First, what may be termed "condensation" relates to the resistance of the alloy to being packed into the cavity by the dentist using typical instruments. It will be clear that an amalgam must have sufficient plasticity when under pressure to enable it to flow into and completely fill all portions of the cavity, thereby preventing the formation of open spaces in the finished filling which could weaken it or permit further decay to the tooth structure. At the same time, the amalgam must not be so fluid as to flow out from beneath the dental instruments during condensation of the amalgam and move up the wall of the cavity. In such situations, a nonuniform degree of packing necessarily results, with poor adaptation to the cavity and increased porosity which weakens the filling and may result in further decay. Thus, one important handling characteristic of an amalgam is its ability to be pressed into a dental cavity to fill all the small openings under the desired condensation pressure, while not being so soft that the dentist cannot adequately compact the amalgam. This condensation pressure may be approximated by an empirical test which will be hereinafter described and which is useful in connection with the present invention.

The second handling characteristic of importance to the dentist is the ability of an amalgam to be carved or shaped in order to finish the exterior surface of the compacted filling. An amalgam also must be of a desired plasticity in order to be satisfactorily carved or shaped. An amalgam may be satisfactorily carved or shaped. An amalgam may be satisfactorily packed into a dental cavity but be difficult to smooth and shape when the packing process is completed. On the other hand, an amalgam which is easy to carve and shape may be difficult to pack properly into a dental cavity. Another empirical test to be described hereinafter may be related to the carving characteristic of the amalgams derived from various dental alloys.

Figure 1:
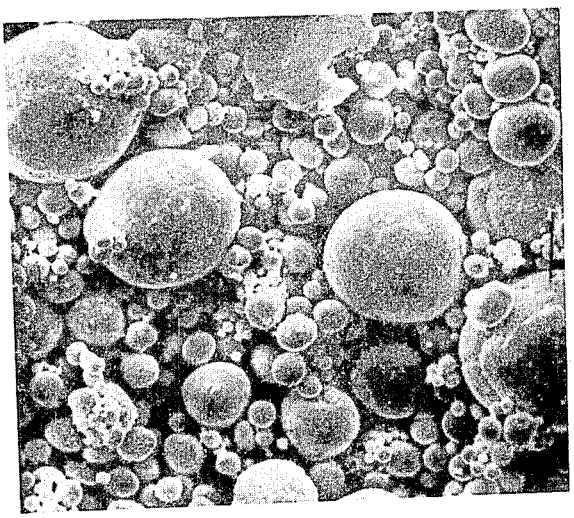
FIG. 1 shows the spherical particles of the prior art corresponding to U.S. Pat. No. 3,871,876.

As described in U.S. Pat. No. 3,253,783 and elsewhere, the gas atomization technique may be used to produce spherical or spheroidal particles from molten dental alloys. Particles are screened after cooling to provide a powdered alloy having aprticles in the size range of about 1 micron to about 65 microns. Larger and smaller particles are separated and recycled to be remelted and recast. Spherical particles such as are illustrated in FIG. 1 have an average surface to volume ratio of about 0.21 $m^2/gm$ as measured by the usual BET apparatus. The randomly-shaped microcrystalline particles of Improved Alloy typically have a BET surface area of about 0.23-0.26 $m^2/gm$. By way of contrast, the flake-like particles commonly used heretofore have a BET surface area of about 0.33 $m^2/gm$. It should be noted that the surface area is related in part to the particle size, thus the values given herein relate to a particle size distribution suitable for dental alloys and as specifically reported hereinafter for the alloy of the invention.

It should be further noted that the surface area measured by the BET apparatus is much larger than the geometric exterior surface of the particles. For example, a perfect sphere would have a surface area only about 10% of that measured for the generally spherical particles of FIG. 1. The additional 90% of the measured surface is evidently due to surface roughness and porosity. Since this additional surface seems less likely to have a large effect on the handling properties of amalgams than the geometric surface, the geometric surface of the particles should be compared rather than the BET surface. However, the geometric surface of the alloy particles has not been measured although it may be approximated by substracting about 90% of the BET value for comparison purposes. In the specification and claims, all surface measurements are those as measured by the known BET apparatus.

Amalgams are produced by mixing mercury with dental alloys of the invention. At the completion of the amalgamation process, the amalgam is condensed into a tooth cavity by a dentist and then the filling is carved or shaped until the amalgam has become so hard that it cannot be worked. This period is typically about six minutes. The dentist packs or condenses the amalgam into the tooth cavity while the amalgam is still soft enough to do so. The pressure required is quite important to the dentist as has been previously discussed and to characterize dental alloys of the invention we have chosen to designate the resistance of the amalgam one minute after amalgamation is complete as the condensation factor. A lower value indicates that an amalgam is stiffer and requires more pressure to pack or condense it into a tooth cavity than an amalgam having a higher numerical value.

The test used to obtain values reported herein for condensation factors may be described as follows. A pellet of dental alloy is mixed with the recommended amount of mercury in an amalgamator for the manufacturer's recommended time. A commercially available Wig-L-Bug Model 5AR manufactured by Crescent Corporation was used in the tests reported herein, although other amalgamators would be acceptable. After the amalgamation is complete, the amalgam is immediately placed on a flat glass plate and covered by another such glass plate and pressed to a one millimeter thickness, as determined by one millimeter spacers placed between the plates. The top plate is removed and measurements are made of the resistance of the flattened amalgam disc during the hardening period. For the measurements reported herein an Instron testing unit model 1101 produced by Instron Corporation was employed. A constant load of five pounds was placed on a two millimeter steel ball in contact with the amalgam. The depth of the indentation made by the ball when the load was applied for fifteen seconds is used as a measure of the resistance of the amalgam. Tests were made at one minute intervals for a period of five minutes, or until no further change in the resistance was measured. The period of time during which measurements were made approximates the time which a dentist uses to fill a tooth cavity and to carve the filling. Test results obtained with prior art dental alloys in spherical and flake form are compared with the dental alloy of the invention in the examples below.

The carvability factor relates to the ability of a hardening dental amalgam to be carved and shaped by dental instruments after it has been compacted. It will be apparent that after the compaction or condensation period (about 2 minutes) the dentist will have a limited time in which to shape or carve the hardening amalgam. A variant of the test previously described is sued to obtain a carving factor. The two millimeter ball loaded by a five pound weight is replaced with a one pound Gilmore needle having a one milli-meter point. The Gilmore needle is normally used for measuring setting rates of cements and plastic materials and has been described in an article by Peyton and Craig in Restorative Dental Materials, 4th ed., 1971. It has been found that the lighter loaded Gilmore needle will fail to penetrate an amalgam after it is sufficiently hardened. The time between the end of the amalgamation process and the failure of the Gilmore needle to penetrate the hardening amalgam may be used as an index of the carvability of the amalgam.

EXAMPLE 1

Figure 2:
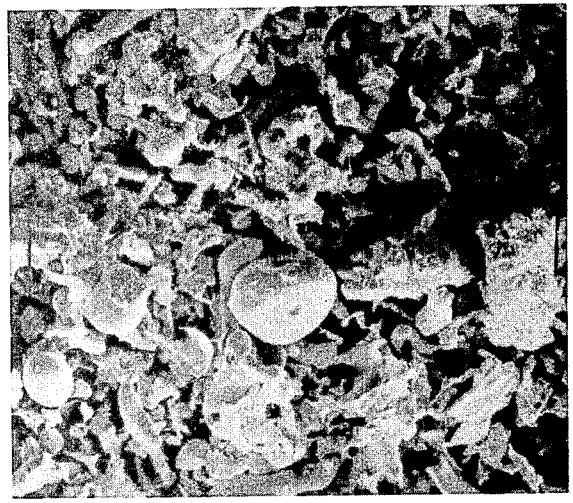
FIG. 2 shows the randomly-shaped microcrystalline particles of Improved Alloy.

A dental alloy is prepared by mixing individual metal powders to provide an overall composition of 58 wt.% Ag, 29 wt.% Sn, 13 wt.% Cu. The powdered mixture is melted and processed in an air atomization apparatus modified to minimize the formation of spherical particles by contacting the molten droplets during the cooling process, thereby producing the randomly-shaped microcrystalline particles of Improved Alloy. The particles formed have a surface area of 0.24 $m^2$/gm. They are sieved to produce a powdered alloy as shown in FIG. 2 and having particles sized within the range of about 1 to 45 microns. The powdered alloy is then pelleted and mixed with sufficient mercury to form an amalgam having an alloy to mercury ratio of 1:1. The amalgam is measured for its resistance to condensation pressure according to the test hereinbefore described.

EXAMPLE 2

A dental alloy is prepared by mixing individual metal powders to provide an overall composition of 58 wt.% Ag, 29 wt.% Sn, 13 wt.% Cu. The powdered mixture is melted and processed in an air atomization apparatus according to U.S. Pat. No. 3,871,876 to produce spherical particles and shown in FIG. 1. The particles have a surface area of 0.21 $m^2$/gm. The particles are sieved to provide particles within the size range of from about 1 to 40 microns and a mean particle size of from about 20 to 26.5 microns. The powdered alloy is then pelleted and mixed with sufficient mercury to form an amalgam having an alloy to mercury ratio of 1 to 1. The amalgam is subjected to the condensation factor test described hereinbefore.

EXAMPLE 3

Figure 3:
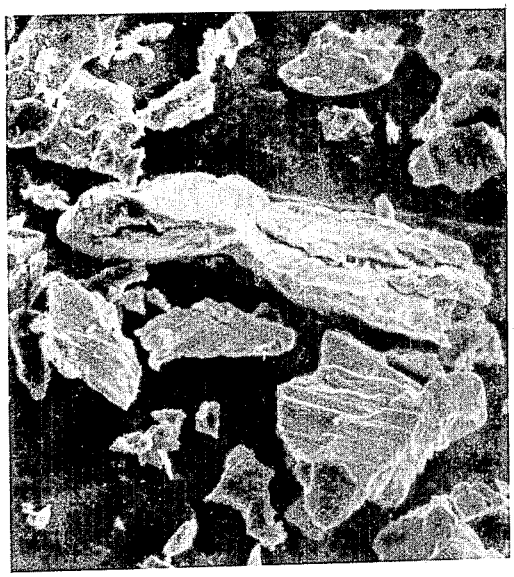
FIG. 3 shows the flake-like particles of the prior art.

A dental alloy is prepared by mixing individual metal particles to provide an overall composition of 68 wt.% Ag, 27 wt.% Sn, 5 wt.% Cu. The mixture is melted and cast in a bar, from which it is cut into flake-like particles as shown in FIG. 3 according to the usual technique of the prior art. The particles have a surface area of 0.33 $m^2$/gm and are within the size range of about 1 to 50 microns. The powdered alloy is then pelleted and mixed with sufficient mercury to form an amalgam having an alloy to mercury ratio of 1.2 to 1. The amalgam is subjected to the condensation factor test described hereinbefore.

EXAMPLE 4

A dental alloy is prepared by mixing 25% by weight of the particles of Example 1 with 60% by weight of the particles of Example 2 and with 15% by weight of the particles of Example 3. The mixed particles have a surface area of about 0.24 $m^2$/gm and are within the size range of 1 micron to 45 microns. The powdered alloy is then pelleted and mixed with sufficient mercury to form an amalgam having an alloy to mercury ratio of 1 to 1. The amalgam is subjected to the condensation factor test described hereinbefore.

Figure 4:
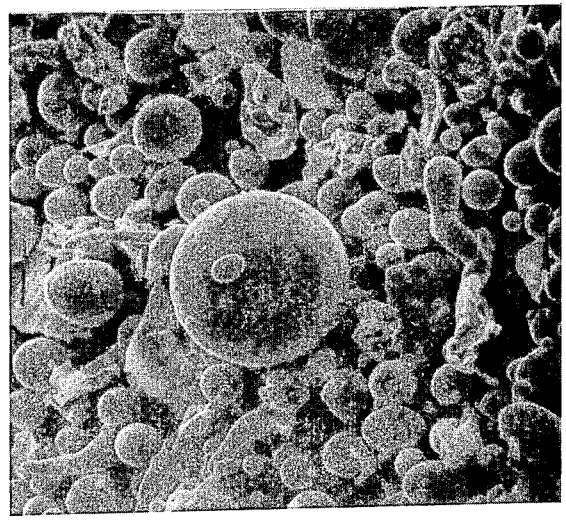
FIG. 4 shows a mixture of the particles of FIGS. 1-3 according to the invention.

The mixed particles of Example 4 and FIG. 4 provide amalgams having handling properties intermediate amalgams made with the spherical particles of Example 2 and the flakelike particles of Example 3. The condensation factors expressed as millimeters indentation after one minute from completion of the amalgamation process are 10.75, 18, 14.0, and 13.0 for the alloys of Examples 1–4 respectively. The spherical particles of Example 2 and FIG. 1 produce an amalgam which is soft when freshly mixed with mercury. As previously indicated, dentists often find amalgams made with spherical particles to be delicate to handle and difficult to condense properly. The randomly-shaped particles (FIG. 2 and Example 1) have a unique morphology which provides handling characteristics similar to those of the flake-like particles of the prior art during the condensation of the amalgam into a tooth cavity. The mixture of spherical particles with randomly-shaped particles and flake-like particles (FIG. 4 and Example 4) provide intermediate handling characteristics which will be experienced by the dentist as a moderately soft amalgam which requires less pressure for proper condensation into a cavity. The combination of Example 4 is only one possible mixture. Clearly, other mixtures could be made to suit the individual requirements of the user. Another satisfactory mixture combines 60% by weight of the particles of Example 1 with 25% by weight of the particles of Example 2 and 15% by weight of the particles of Example 3. The surface area of such a mixture is about 0.25 m²/gm and the size distribution is within the range of about 1 micron to about 45 microns. An amalgam made of such a mixture will be generally firmer than the mixture of Example 4 and its condensation factor after one minute would be about 12.5 millimeters.

The particles of Examples 1 and 2, having a relatively high copper content overall and a higher than average silver and copper content at the surface than in the interior of the particles are corrosion resistant and may be combined in any proportions found desirable to adjust the handling characteristics of amalgams made from alloys of the invention. The relatively high silver and low copper content of the flake-like particles of Example 3 are not so resistant to corrosion. Consequently, the flake-like particles may be included in an alloy according to the invention as desired to adjust handling characteristics of amalgams made therewith, but limited to a maximum of 25% by weight of the alloy in order to retain the corrosion resistance of the other two particles. The flake-like particles typically will have a composition of about 55% to 75% by weight silver, 20% to 40% by weight tin, 0% to 10% by weight copper and 0% to 2% by weight zinc.

The carving period (typically 2 to 5 minutes after amalgamation) represents the time period when the dentist shapes the compacted filling to suit the patient's bite. After a certain period the amalgam becomes unduly hard and can no longer be worked with the usual dental instruments. After about one hour a typical amalgam has reached substantial strength and can withstand the pressure of normal use. Another test may be used to discriminate between amalgams made from alloy particles of various shapes. Measurements of the three particles in the preceding examples made by substituting a Gilmore needle for the two millimeter ball as previously described, give the following results.

TABLE I

| Particle Type | Carving Factor Time, minutes - Penetration Ceased |
|---|---|
| Spherical (Ex. 2) | 4.15 |
| Microcrystalline (Ex. 1) | 3.15 |
| Flake-like (Ex. 3) | 2.15 |
| Mixed particles (Ex. 4) | 3.50 |

The above results indicate that spherical particles can be carved with less force and for a longer time than the randomly-shaped microcrystalline particles, which have the same advantage over flake-like particles. The mixture of particles, as would be expected, can be carved with less force for a longer period than the amalgams made with the flake-like particles of Improved Alloy (Example 1) but the mixture is firmer and hardens quicker than amalgams made with spherical particles.

Mixing particles according to the invention provides a means by which the handling characteristics of dental amalgams may be adjusted to suit the requirements of the individual user. At the same time, when the flake-like particles are limited to a maximum of 25 weight percent, the resulting mixtures are found to have satisfactory corrosion resistance.

Alloy particles are sieved to provide a typical particle size distribution as follows:

| Microns | Wt.% |
|---|---|
| 52–75 | 0.2 to 1.4 |
| 44–52 | 1.4 to 12.2 |
| 38–44 | 1.6 to 8.9 |
| 30–38 | 20.9 to 24.6 |
| 20–30 | 26.1 to 35.7 |
| 10–20 | 24.0 to 35.4 |
| 1–10 | 3.6 to 7.2 |

The mean particle size is typically 20 to 26.5 microns. Although some variation about the above typical size distribution may be made to adjust the handling characteristics, an amalgam prepared with particles having a significantly different size distribution from that given above will have handling characteristics differing from those reported herein. In general, the smaller the average particle size, the firmer the amalgam will be and the shorter the working time.

As previously discussed, the surface area of the alloy particles of the invention having the size distribution as given above will be found to have a BET surface area between those of the component particles, namely from about 0.24 m²/gm to about 0.27 m²/gm. With other size distributions, the surface to volume ratio may be wider.

Particles may be used directly to form amalgams, especially if employed in pre-mixed dental capsules. Often the particles are pelletized for use in dispensers designed to provide the desired amount of mercury needed to amalgamate with the pelleted alloy. The pelletizing process has been found to alter the handling properties of the resulting amalgam, generally providing a dry and less plastic amalgam than if the powdered alloy were used directly. It has been found that by heat treating the pellets in a vacuum or under an inert atmosphere (e.g., argon, nitrogen) for a suitable time, the mechanical properties and useful working time of the alloy can be returned to their original and more desirable values. Typically a vacuum of about ten microns (0.01 mm Hg absolute pressure) has been found to be acceptable, the determining factor being the need to avoid oxidation of the metals with the consequent degradation of physical properties and corrosion resistance. The heat treatment is carried out typically between 100° and 700° F. (37.8° to 370° C.) as required until the handling characteristics of an amalgam made from the pellets matches those of the unpelleted powder, as measured by the condensation and carving factors.

Generally, at least about 90% of the particles of the alloy of the invention will fall within the size range of from about 10 to 52 microns. Particles of a size greater than 52 microns should comprise not more than about 1.4% by weight of the alloy particles. With particles larger than about 52 microns, such oversized particles could pose difficulties in filling small apertures in a tooth. The lower limit of particle size is determined by the fact that with very small particle sizes the desired effect provided by the defined specific shape of the particles of the invention is lost. Further, very fine particle sizes of the alloy use up a proportionately greater amount of mercury in the amalgam and tend to increase the proportion of mercury beyond the desired limit.

Obviously, particle range sizes expressed herein are maximum ranges; the actual particle size range of specific embodiments of the invention may fall within a narrower range encompassed by the broadly stated ranges.

The foregoing discussion of the preferred embodiments of the invention is not intended to limit the scope of the invention, which is defined by the claims which follow.

What is claimed is:

1. A corrosion-resistant dental alloy mixture for use as a filling for dental cavities after amalgamation with mercury, consisting essentially of a substantially uniform mixture of a first corrosion-resistant alloy comprising a mixture of silver, tin and copper, said first alloy being in the form of spherical particles having a mean particle size of from about 20 to 26.5 microns, and further having a particle size distribution such that substantially all of said particles fall within a particle size range of from about 1 to 75 microns, said spherical particles having a surface area of about 0.21 $m^2/gm$, a second corrosion-resistant alloy comprising a mixture of silver, tin and copper, said second alloy being in the form of randomly shaped particles having a mean particle size of from about 20 to 26.5 microns, and further having a particle size distribution such that substantially all of said particles fall within a particle size range of from about 1 to 75 microns, said randomly shaped particles having a surface area which, exclusive of both spherical particles and flake-like particles as herein defined, ranges from about 0.23 to 0.26 $m^2/gm$, and a third alloy comprising a mixture of silver, tin and copper, said third alloy comprising flake-like particles having a mean particle size of between about 25 and 30 microns, and further having a particle size distribution such that substantially all of said particles fall within a particle size range of from about 1 to 75 microns, said particles having a surface area of about 0.33 $m^2/gm$, said third alloy comprising not more than about 25% by weight of the dental alloy mixture.

2. The corrosion-resistant dental alloy mixture of claim 1 wherein said first and said second alloys comprise from about 47 to 70 percent by weight of silver, from about 20 to 32 percent by weight of tin, and from about 7 to 27 percent by weight of copper.

3. The corrosion-resistant dental alloy mixture of claim 1 wherein said third alloy comprises from about 55 to 75 percent by weight of silver, from about 20 to 40 percent by weight of tin, and up to about 10 percent by weight of copper.

4. The corrosion-resistant dental alloy mixture of claim 1 comprising from about 25 to 60 percent by weight of said first alloy, from about 25 to 60 percent by weight of said second alloy, and from about 15 to 25 percent by weight of said third alloy.

5. A dental amalgam comprising a combination of the corrosion-resistant dental alloy mixture of claim 1 with mercury.

6. The dental amalgam of claim 5 comprising about 1 part by weight of mercury for each part by weight of said corrosion-resistant dental alloy mixture.

7. The corrosion-resistant dental alloy of claim 1 wherein at least about 90% by weight of said particles fall within a particle size range of from about 10 to 52 microns.

8. The corrosion-resistant alloy of claim 1 including about 25 to 60 percent by weight of said second alloy.

* * * * *